Figure 1:
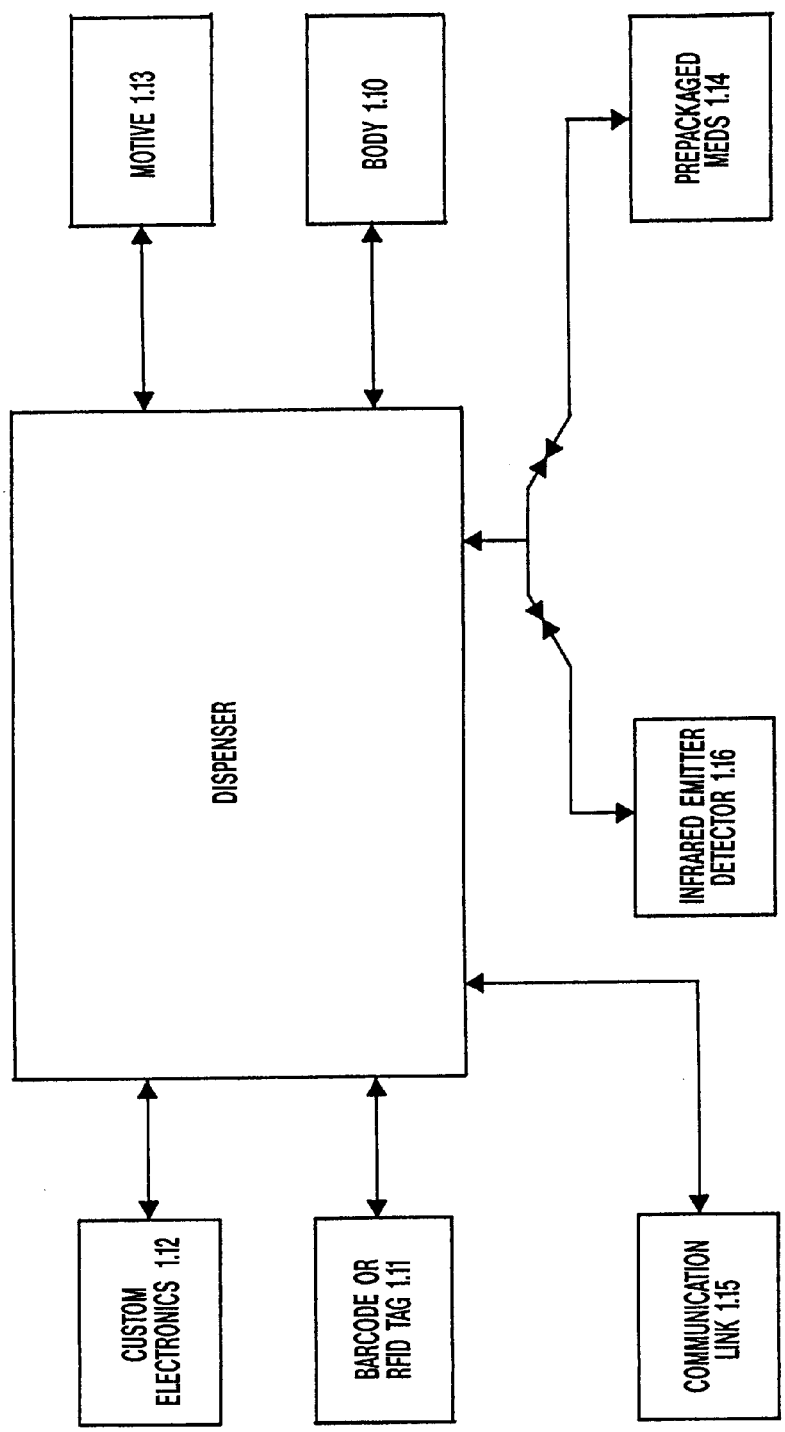

United States Patent [19]

O'Brien

[11] Patent Number: 5,963,136
[45] Date of Patent: Oct. 5, 1999

[54] INTERACTIVE PRESCRIPTION COMPLIANCE AND LIFE SAFETY SYSTEM

[76] Inventor: Charles Terrence O'Brien, 1451 Parkview Ter., S., Algonquin, Ill. 60102

[21] Appl. No.: 09/115,650

[22] Filed: Jul. 15, 1998

[51] Int. Cl.⁶ .................................................. G08B 21/00
[52] U.S. Cl. .................................. 340/573.1; 340/825.36; 364/400; 379/38
[58] Field of Search ........................... 340/573.1, 825.36; 364/400; 379/38

[56] References Cited

U.S. PATENT DOCUMENTS 5,512,935  4/1996  Majeti et al. ............................... 348/9
5,623,242  4/1997  Dawson, Jr. et al. ............... 340/311.1
5,852,408  12/1998  Christiansen et al. ............. 340/870.09

*Primary Examiner*—Glen Swann
*Attorney, Agent, or Firm*—Mathew R. P. Perrone, Jr.

[57] ABSTRACT

An interactive prescription compliance, and life safety system provides remote and on site verification of procedures related to the health status of a person, including taking of medicines, responsiveness to queries, and attendance of health care and service providers in the home by providing for signals to and from a person's location, with alarm activation when a deviation from a preprogrammed procedure occurs.

7 Claims, 7 Drawing Sheets

INTERACTIVE PRESCRIPTION COMPLIANCE AND LIFE SAFETY SYSTEM

BACKGROUND OF THE INVENTION

This invention relates to a device and a procedure for providing compliance with the correct taking of Prescription Drugs through an "interactive compliance system" which incorporates third party monitoring and interactive participation by the user of said drugs. Medical monitoring and personal safety and life safety are additional benefits to this invention.

PRIOR ART

While prescription drugs are modern miracles in preserving and extending a person's life, not taking prescriptions as required (non-compliance) has become a major health problem. Additionally people living alone, particularly the elderly, are subject to other incidents such as falls and drug reactions rendering them unable to call for help.

Non-compliance in prescription drug taking is putting an enormous strain on the entire health care system today. Estimates of cost to the United States economy range from 50 to as high as 100 billion dollars per year. It is estimated 17% of all Emergency Room visits are the direct result of a prescription drug misadventure (non-compliance). Other results of non-compliance include hospital and nursing home admissions as well as lost wages and lower productivity.

As the population ages, compliance becomes a source for even more concern. Population experts say by the year 2003, 83 million Americans will be over the age of 50, and by the year 2010, that figure will be over 100 million. Currently no system exists to assure compliance in the taking of prescription drugs. Pager systems such as U.S. Pat. No. 5,623,242 to Dawson and Bryon, Apr. 22, 1997, provides that a signal is sent from a central data base containing all the pertinent information of the prescription to an individual pager reminding them to take the medication. However, such a system does not insure the medication has been taken. To ensure compliance, an interactive response should be sent back to the central database by the individual taking that specific medication. While drug compliance will go up using the pager system, patient response to the pager signal, or other alarm type signals, ensure an even higher compliance rate.

In-home safety and security is a growing concern for all people not just Americans. Safety and security companies have traditionally provided companies and wealthy individuals with services such as CCTV (closed circuit television), fire and burglar alarm monitoring and recently interactive video. Currently systems specifically for the home (wired or wireless) are now available. These services include smoke, fire, burglar, water, temperature, keyless door entry and carbon monoxide detection. Research in this area show specific patents but no central controller patent. U.S. Pat. No. 5,673,016 to Lutes Sep. 30, 1997, describes a visitor information system. While the communication links are available between the home or institution and safety/security companies, "an Interactive Prescription Compliance System" is not offered.

Wireless alarm systems for compliance safety and security simply are not in the U.S. Patent database. U.S. Pat. No. 5,625,338 to Pildner Apr. 29, 1997, is a wireless keypad to control communications to a control panel for entrance and exit control. U.S. Pat. No. 5,698,427 to Arthur, Jan. 28, 1997 appears to be a burglar alarm system.

Continuing with in-home systems; pill or medication dispensers for home use such as U.S. Pat. No. 5,405,011 to Haber Apr. 11, 1995, U.S. Pat. No. 5,575,392 to Cutler Nov. 1996, and U.S. Pat. No. 5,641,091 to Danes/Havar Jun. 24, 1997, do not incorporate the latest technologies such as bar codes or RFID tags, but rather are mechanical in nature. U.S. Pat. No. 5,609,268 to Shaw Mar. 11, 1997, is a microprocessor controlled pill dispenser, but it too fails to incorporate interactivity with the user and does not use other interactive components such as bar code and RFID technology. Drug compliance can now be assured with such dispensers.

Bar codes and RFID tags are by their very nature wireless interactive or active devices. Bar code readers and RFID tag readers by design could be wired to a fixed point or wireless. U.S. Pat. No. 5,640,002 Ruppert Jun. 17, 1997, is a portable (wireless) RFID tag and bar code reader for grocery stores. U.S. Pat. No. 5,646,592 to Tuttle Jul. 8, 1997, is an RFID tag for security of containers such as suitcases. U.S. Pat. No. 5,602,380 to Bishop Feb. 11, 1997, is a line of sight bar code scanner/reader using infrared technology. U.S. Pat. No. 5,721,421 to Van Doukeluur Feb. 24, 1998, is a wireless bar code reader used for identifying shelf tags. The required information is then transmitted to a terminal processed and then retransmitted to an RF to a base station. All these systems have the following features in common: (1) merely state of the art technology, (2) not a consumer product and interactive prescription compliance device. Therefor, drug compliance is not an obvious benefit of these systems.

U.S. Pat. No. 5,700,998 to Palti Dec. 23, 1997, uses bar code technology. A bar code is printed on pills and a bar code assigned to a patient. If the patient's bar code does not match the pill bar code, an alarm is generated indicating a mismatch of patient and medication. This system appears to be institutional in nature, as does U.S. Pat. No. 5,713,487 to Coughlin Feb. 3, 1998, an automated medication system using bar codes and manipulating arms. U.S. Pat. No. 5,564,803 to McDonald Oct. 10, 1996, is a portable nursing center utilizing bar codes and a keyboard data entry system to open specific drawers containing medications. While these systems seem to ensure some form of compliance, none provide for personal safety and security.

Cable Set Top Boxes are becoming commonplace in homes, assisted living centers, retirement centers, nursing homes, hotels and adult day care centers. U.S. Pat. No. 5,512,935 to Majeti Apr. 30, 1996, appears to be a cable set top box which flashes messages to individuals on personal computers. U.S. Pat. No. 5,649,283 to Goller Jul. 15, 1997, is a device used to ensure the correct programming is being received at the television set of a consumer. U.S. Pat. No. 5,631,903 to Dianda May 20, 1997, is a cable set top box which controls television sets. U.S. Pat. No. 5,727,052 to Sizer Mar. 10, 1998, is a system to record and display information at a remote location using that location's recording unit over a telephone network. Cable set top boxes today do not have the capabilities of receiving wireless data from sensors placed in the home or institutional settings. They also do not have bar code or RFID readers or telephone jacks to reach a customer service center via the PSTN or the cellular network. Until now there has not been a need for such features.

If a means were developed to remind patients to take medication correctly or at prescribed intervals whether at home or away, plus add the feature of assuring compliance through interactive response, emergency room visits, hospital or nursing home admissions would be greatly reduced. Couple the drug compliance feature with medical monitoring such as, but not limited to, electrocardiogram, oxygen and renal, plus in home or room safety and security. Medicare, Medicaid, third party insurance and personal financial costs would be reduced dramatically. An additional benefit would be the monitoring time spent by visiting nurses through electronic time cards. The visiting nurse enters in a PIN code identification number upon arrival and repeats the procedure upon departure, thus verifying and recording time spent with the patient, eliminating a major source of Medicare fraud. Other service providers, such as therapists, oxygen delivery person or Meals-On-Wheels people, could also be assigned a PIN code identification number. All of the data would be stored in the Customer Service Center and available to the caregivers, government programs (Medicare/Medicaid) doctors and insurance companies for each patient.

My Interactive Prescription Compliance System uses the PSTN, bar code readers, wireless monitoring devices and a cable set top box like console. By PSTN is meant phone system telephone network. Provisions in the console have incorporated, through interconnections and stuffing options, to add automated prescription dispensers, cellular phone lines, cable and broadcast TV inputs and pager or palm pilot-like devices.

Functionality of all of these features described have been developed in theory and through custom electronics work in my Interactive Prescription Compliance System. Presently the research of existing systems reveals no clear complete and total embodiment of the proposed patent I have submitted. The cost for the care of terminally ill patients such as AIDS and cancer patients, plus the growing aged population, would become substantially less with the use of my Interactive Prescription Compliance System. Use of this system would reduce the chance of non-compliance by over-medication.

ADVANTAGES OF INTERACTIVE PRESCRIPTION COMPLIANCE SYSTEM PATENT

A. Prescription drug compliance increased
B. Utilizes new technology combined with existing devices
  1. ASIC Semiconductors (application specific integrated circuit)
  2. Bar code scanners and readers
  3. RFID tag scanners and readers
  4. Bar code labeled or RFID tagged prescription vials or microprocessor controlled prescription dispensers labeled or tagged with same
  5. Use of 433 MHZ and 900 MHZ band for home sensor and cordless phone
  6. Use of 125 KHZ, 13.56 MHZ and 2.45 GHZ band for RFID tags.
C. Interactive response required by patient to central station
  1. No response to reminder—patient is called
  2. Still no response caregiver is dispatched to site
D. Personal safety and security
  1. Fire, burglary, water, temperature, electricity, carbon monoxide alarms, panic buttons (Help Me I've Fallen Down), perimeter monitoring (Alzheimer patient) keyless entry systems, interactive video/audio
E. Visiting nurse and other caregiver monitoring (Meals-On-Wheels, therapists, etc.)
F. Medical monitoring electrocardiogram, renal, oxygen, etc.
G. Individual patient monitoring through Interactive Video
H. Central station monitoring and database storage of compliance or noncompliance
I. Reports of all activities available to all interested parties

INTERACTIVE PRESCRIPTION COMPLIANCE AND LIFE SAFETY SYSTEM DRAWINGS

FIG. 1 Rendering of Interactive Prescription Compliance System Drug Dispenser.

Figure 2:
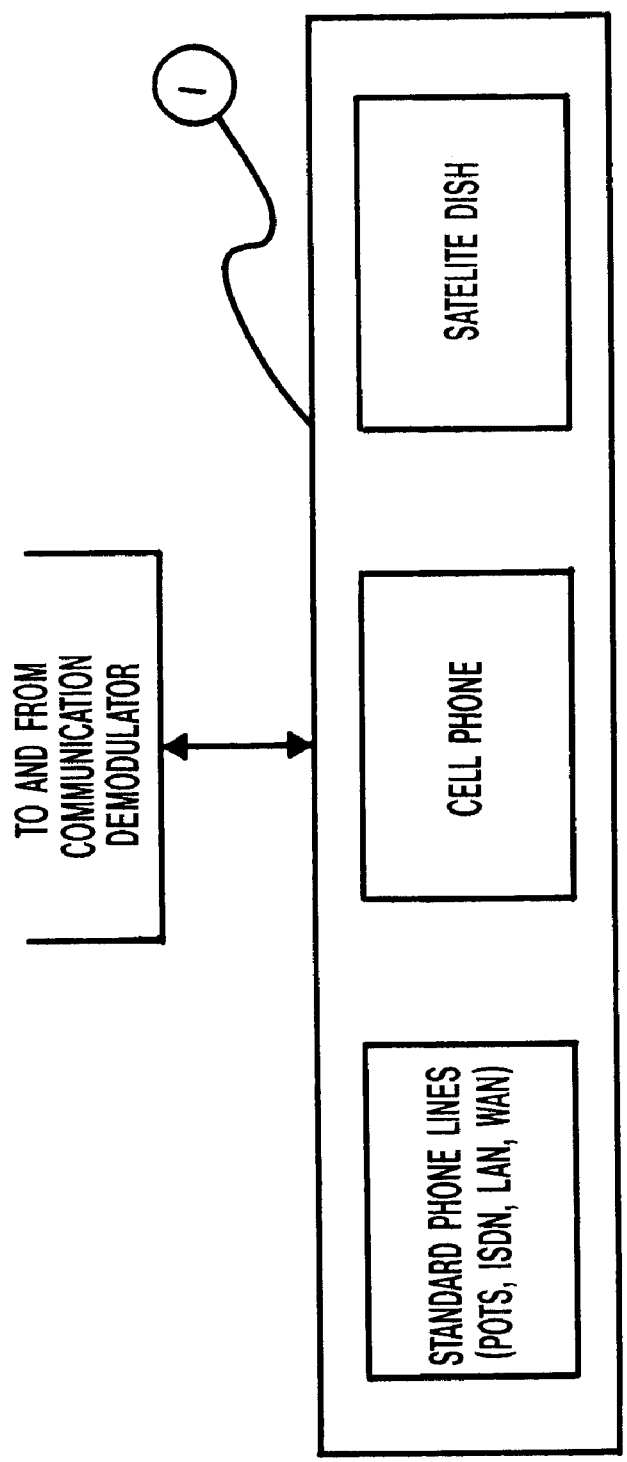
Figure 5:
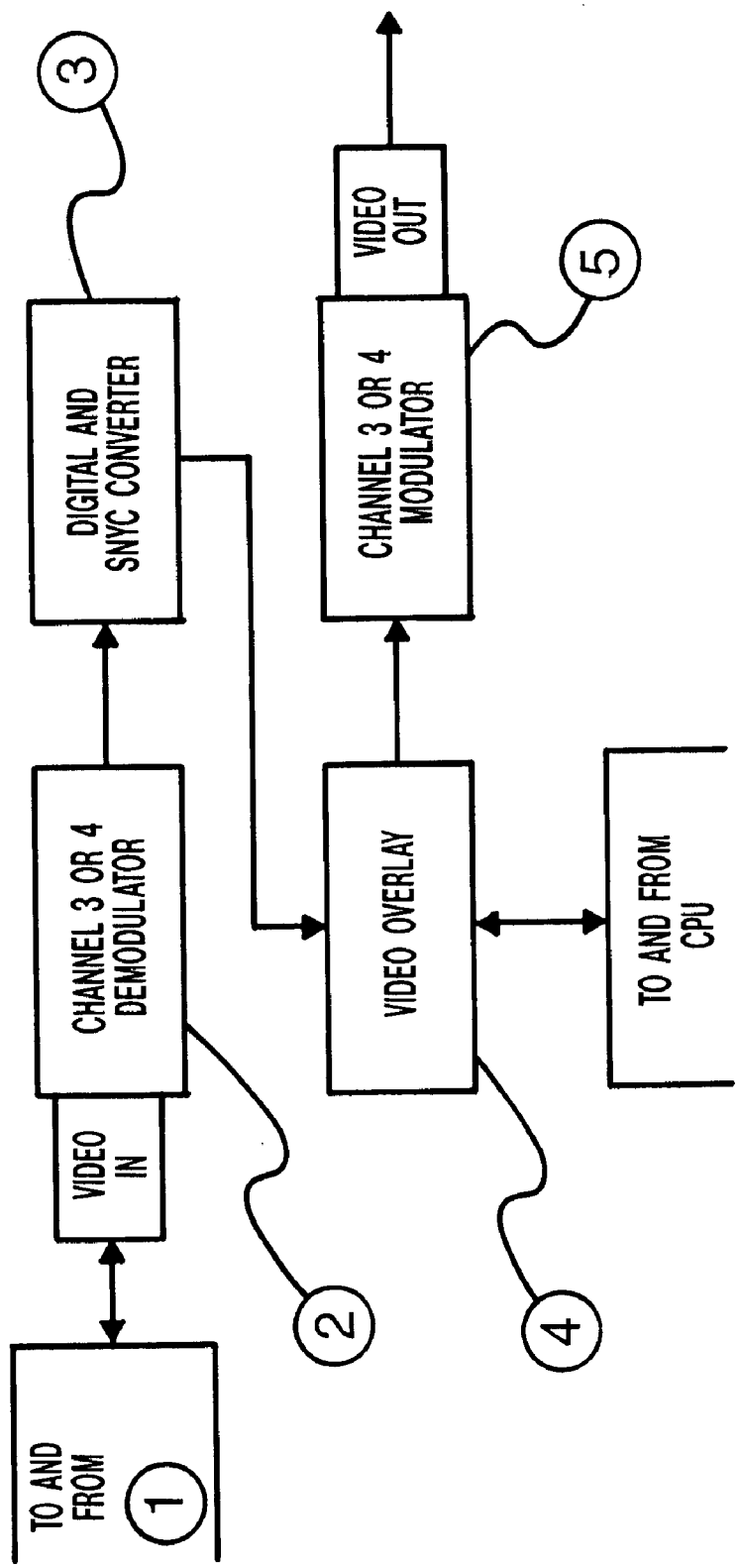
Figure 6:
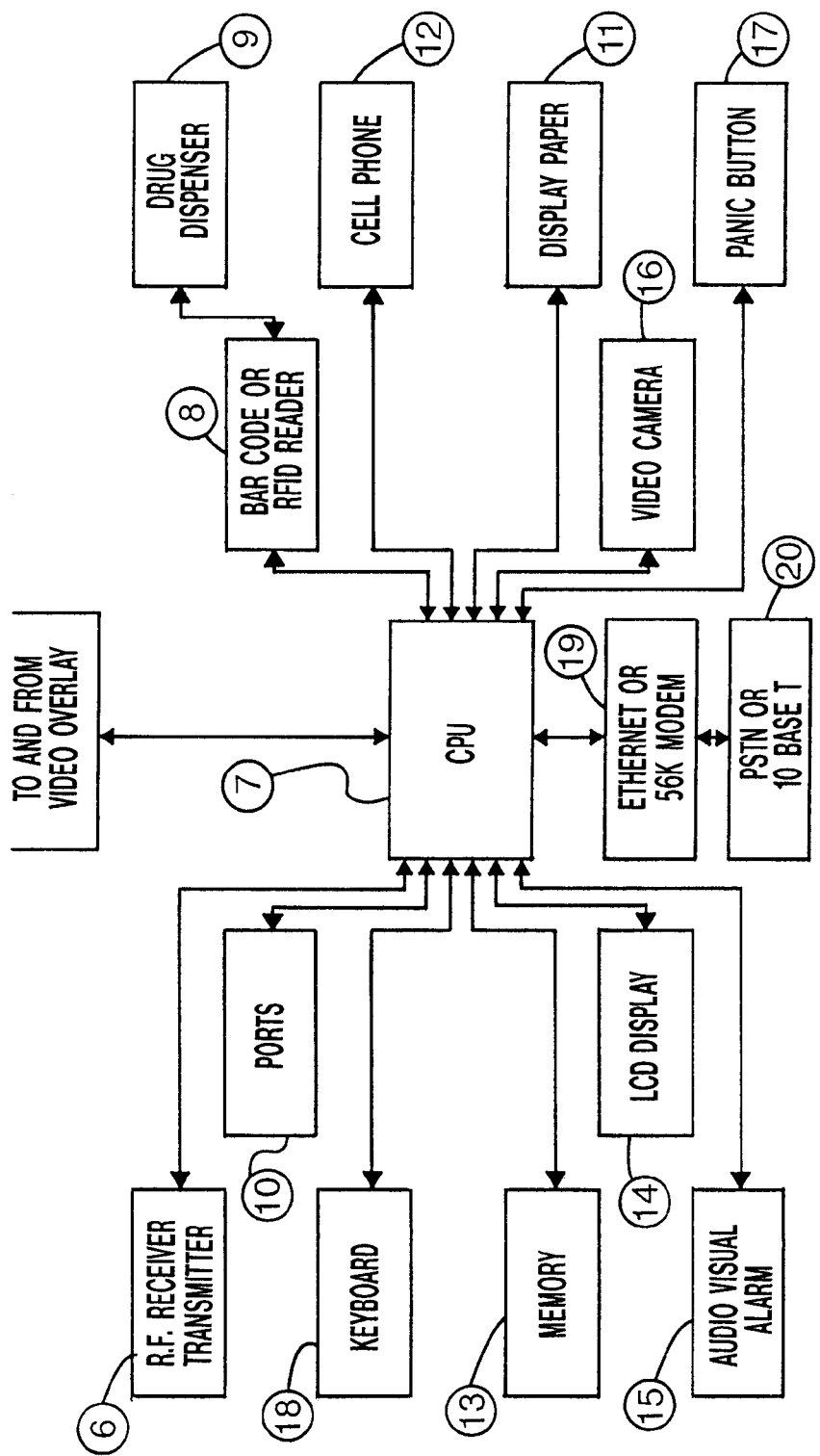

FIG. 2, FIG. 5 and FIG. 6 Flowchart of Interactive Prescription Compliance System Box showing Prescription Dispenser utilizing bar code or RFID tag technology also shown optional Palm Pilot or Beeper-like device, optional video camera, optional cellular phone, wireless life safety devices and wireless panic buttons.

Figure 3:
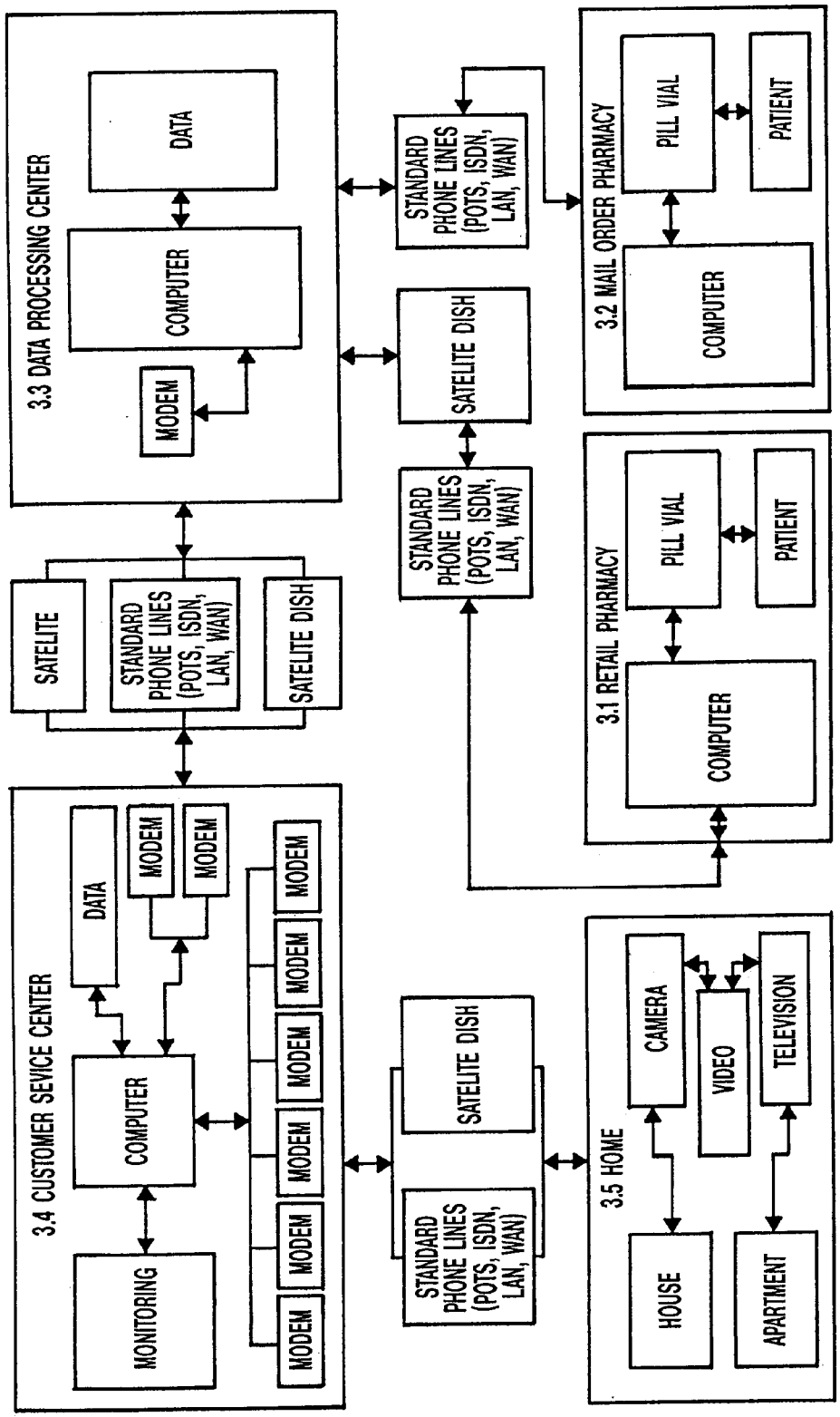

FIG. 3 Home Interactive Prescription Compliance System Architecture with Compliance Set Top Box and Interactive Audio Visual Option.

Figure 4:
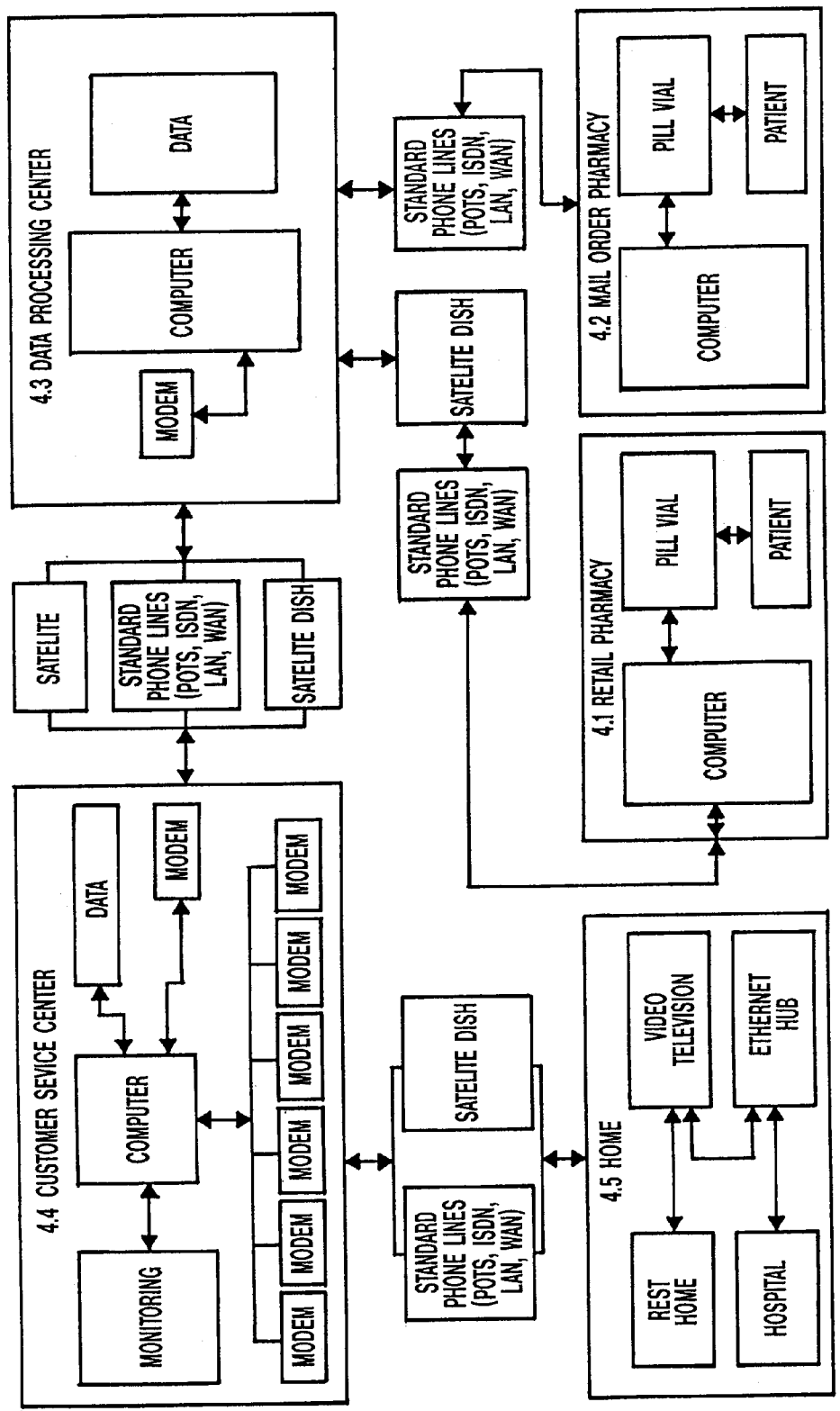

FIG. 4 Institutional Interactive Prescription Compliance System Architecture with Compliance Set Top Box and Interactive Audio Visual option.

Figure 7:
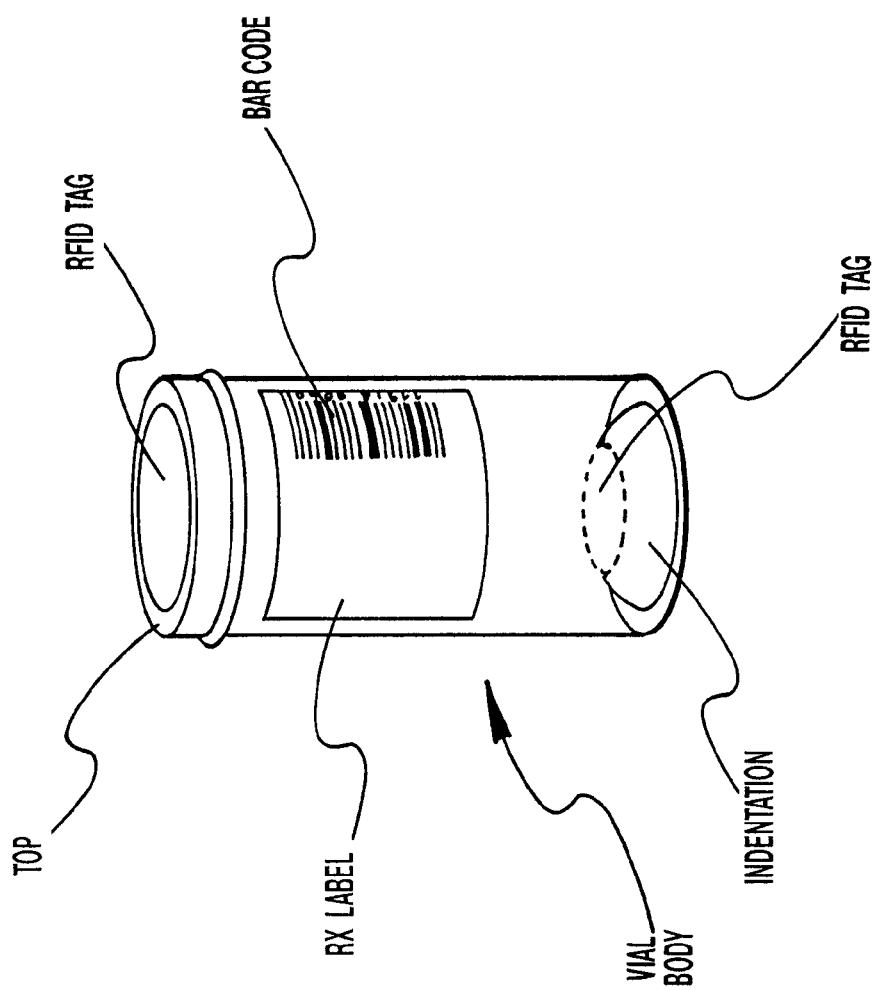

FIG. 7. Prescription vial bar coded or RFID tagged.

Description of FIG. 1—Interactive Prescription Compliance System Drug Dispenser.

Referring to FIG. 1, major components consist of body 1.10 which conforms to all applicable standards for UL 2034 specifications. Bar code or RFID tag 1.11 affixed to housing by means of printed bar code label or preprogrammed RFID tag. Information contained in bar code or RFID tag 1.11 will be used to activate some, but not all command controls in the Customer Service Center (FIGS. 3.4 and 4.4 to Interactive Prescription Compliance System Set Top Box FIG. 2.) Custom electronics 1.12 are microprocessor based utilizing standard cell and ASIC designs and receiver input from compliance set to box (FIG. 2) by means of a communications link present via a connector which is part of the Interactive Prescription Compliance Dispenser Stand 1.15 which affixed to interactive Prescription Compliance Set Top Box FIG. 2. Custom electronics microprocessor based 1.12 processes data received from Customer Service Center, FIGS. 3.4 and 4.4, and activates miniature stepper motor and spindle 1.13. A prepackaged single dose serrated medication packet spooled containing at least a one week supply of meds 1.14 is then dispensed at correct intervals, one packet at a time from data supplied from custom electronics 1.12 and rotated out of dispenser by motor spindle 1.13. In the case of multiple prescription drugs prepackaged spool of meds 1.14 will be packaged according to prescription directions provided by patients doctor and filled at mail order facility, FIG. 3.2 and 4.2. Each individual prepackaged medication packet shall be of cellophane-like material and have printed on it patient name, drug name, doctor's name, other information could be added as required. An extension cord-like cable of sufficient length could be affixed to the dispenser allowing a bedside or chair side use of said dispenser. It is possible to completely control this dispenser by the Customer Service Center. This is accomplished by control signals sent by the Customer Service Center dispensing packets or "locking" the dispenser. The dispenser is CPU based with flash memory, which allows complete control.

Description of FIG. 2, FIG. 5, and FIG. 6—Interactive Prescription Compliance Console.

Referring to FIG. 2 (References to FIG. 2 include FIG. 2, FIG. 5, and FIG. 6, the completely Interactive Prescription Compliance Console is a microprocessor based system which utilizes cable set top box technology plus unique features relating to compliance and safety for the individual user.

FIG. 2 illustrates in block diagram form the theory of operation beginning with normal broadcast cable television signal 1 received by the users' Compliance Console and in the case of a cable signal are then processed by the channel 3 broadcast signal or demodulator 2. Broadcast signal or demodulator 2 is designed with circuitry to directly pass signal to the user's television set. Continuing with FIG. 2, the cable signal is demodulated then digital and synchronous converter and passed to the channel 3 modulator 5. The cable signal is then modulated by modulator 5 and sent to user's television. Channel selection is accomplished by use of standard wireless infrared emitter/detection circuit (remote or clicker). The cable broadcast signal could be completely independent of the systems CPU 7 and the video overlay circuit 2.4.

More particularly, an appropriate group of parts for carrying out the functions of the interactive prescription compliance and life safety system of this invention are as follows:

SET TOP BOX STANDARD FEATURES
1. CPU
2. Memory Dram and Flash
3. RF (radio frequency) Receiver
4. ports including RS232, PCMCIA, VGA, Smart card
5. PS/2 Type Key board with alarm and reset buttons
6. Liquid Crystal Display
7. Video Overlay Circuit
8. Audio or Visual Alarm
9. Bar Code or Radio Frequency Identification Tag (RFID) Reader or Scanner
10. Drug Dispenser Port
11. Modem (preferably 56 K or better)
12. Ethernet 10 Base T Converter
13. Auto Dialer
14. Stand-by Battery Power 24 Hr. Min.
15. Priority Interrupt SET TOP BOX OPTIONAL FEATURES
1. Wireless Safety and Security Devices
   a. Fire Alarm
   b. Burglar Alarm
   c. Temperature Sensor
   d. Carbon Monoxide Detector
   e. Water Sensor
   f. Electricity Sensor
   g. Panic Buttons
   h. Perimeter Limiting Alarm (Alzheimer Patient Wandering Off)
   i. Video Camera
   j. Keyless Door Entry
2. Display Pager
3. Cellular Telephone
4. Drug Dispenser
5. Interactive Audio or Video medical monitors, including but not limited to, electro cardiogram, renal function, oxygen and blood pressure.

The System (FIG. 2) will contain DRAM and FLASH Memory 13 sufficient enough to allow for the operation of all options: RF Receiver/wireless monitors 6, display pager 11, Cellular Phone with display 12, interactive video 16 and Panic Button 17. The Flash Memory section of the system 13 also allows the Customer Service Center FIG. 3 section 3.4 and FIG. 4 Section 4.4 to communicate new prescription information and also to allow control by the Service Center to turn on/turn off or reprogram other features of the system, including the ability to lock the Prescription Dispenser System (FIG. 1).

The Interactive Prescription Compliance Console has been designed with multiple unique features to assure maximum prescription drug compliance and safety. The CPU 2.7 has been programmed with a unique address (PIN code) also configured to accept packetized data through circuity designed in section 2.20 which interfaces with the PSTN or a 10 BASE T system. The 10 BASE T system is part of the Ethernet system. A bar code/RFID tag reader 8 (FIG. 6) has been incorporated with the interactive system. It is required to correctly identify the user and the user's bar code or RFID tag of the prescription vial, FIG. 6, and/or also to identify the user and the users bar code or RFID Tag of Drug dispenser 9. The Drug Dispenser is connected to the Interactive Prescription Compliance System through a cable and RS232 port like connection which is present on both the Set Top Box (FIG. 2) and Drug Dispenser and stand (FIG. 1).

Interactive Compliance could be accomplished by user removing serrated package of medication breaking the infrared emitter detector circuit dispenser 1.16. The meds are automatically dispensed per SIG (dosage and intervals) recommended by the doctor and programmed in the Customer Service Center. That circuit interruption generated a signal to dispenser custom electronics 1.12 to Interactive Compliance Reminder System Set Top Box CPU 7 to Customer Service Center which stores in its database that the meds package has been removed and compliance has occurred.

Another Interactive Compliance method would be to pass the pill vial (FIG. 7) in front of the bar code/RFID tag reader after alarm reminder signal has been set by Customer Service Center to users, the Interactive Prescription Compliance Console reminding user to take medication. Such action taken by user (bar code/RFID Swipe) generates a signal to CPU 7 back to Customer Service Center identifying which prescription medication user is about to ingest. If the bar code RFID tag information on Medication Pill Vial (FIG. 7) does not match medication information at Customer Service Center, user is immediately notified by telephone or other means. If information supplied matches, Customer Service Center records the Compliance event in its database. An extension cord like cable could be affixed to reader allowing for bedside or chair side use.

If the user does not respond to the alarm reminder signal after two (2) attempts by the Customer Service Center, the primary caregiver would be notified. This action would ensure the user would be in compliance. Dates, times of non-compliance, as well as caregiver notification are recorded in the Customer Service Center data base.

The Keyboard 18 of the system will be a conventional cable set top box PS2 type and be accessorized with alarm buttons having priority interrupt on the users telephone line and direct dial capabilities to the fire and police departments (911), Customer Service Center and to the designated caregiver. A compliance button could also be added which would be depressed by the user. It would be depressed only after the user had swiped the prescription vial past the bar code (RFID) tag reader and matched the data present in the Customer Service Center. Pressing the compliance button would generate a signal back to the Customer Service Center that complete compliance had occurred. These buttons will be marked in accordance with symbols complying with the Americans with Disabilities Act. Additional auxiliary buttons, will be able to be programmed by the user to call other entities on a priority basis such as a doctor or next-door neighbor. The keyboard will be physically enlarged and back light to allow for easier use by the sight impaired or the physically handicapped. The keyboard 18 would also be the means of having visiting nurse, therapist, caregiver, meals on wheels or medical equipment provider record when these services and goods were provided. An identification number (PIN code) would be assigned to these individuals. Log-in and log-out entries would be required of these service providers to alert the Customer Service Center of the dates and times service and goods were provided to user. Failure to log-in or log-out by these individuals would result in an alarm condition at the Customer Service Center and notification of same would be conveyed to the users' primary caregiver.

The color liquid crystal display 14 will be of sufficient size and back light allowing the user of average or slightly less than average eye sight to see the Interactive Compliance Reminder Message. "Mrs Jones 3 PM Tuesday, March 17 take your blood pressure medication." Other information could be displayed showing the user the size shape and color of the medication to be taken or special instructions like— "take with meal" "take with milk". This display could also be an unlit black and white LCD.

Audio visual alarms 15 are also a permanent feature of the Interactive Prescription Compliance System. As the drug compliance message is generated from the Customer Service Center and transmitted to the users Set Top Box LCD Displays an additional sub-carrier signal activating the audio/visual alarm. It consists of a piezoelectric like speaker with an audio output level of approximately 85 DB and a flashing LED. The audio alarm and flashing LED will alert user that a predetermined time has elapsed and the user is required to take more medication. This alarm unit will continue intermittently beeping and flashing for a period of three minutes or until the compliance button has been pressed. Failure to press the compliance button within three minutes results in a system reset and the Compliance Signal is retransmitted from the Customer Service Center and the three minute alarm is again sent to the user. Failure for a second time to respond by the user within three minutes, generates an alarm condition at the Customer Service Center. A telephone call is then placed by the Customer Service Center to the user. Failure by the user to respond results in the Customer Service Center contacting the authorities to check condition of user. This audio/visual alarm could be wired with an extension cord-like cable of sufficient length to allow it to be placed next to a bed, chair or central location. This alarm could also be wireless.

The Video overlay 4 of the Interactive Prescription Compliance System allows compliance reminder special instructions and even advertising to be scrolled across the bottom of the users television set. This messaging would not disturb the current programing but would rather be like a weather service "Severe Thunderstorm Warning" generated by the Customer Service Center. "Mrs. Jones, it is time to take your blood pressure medication, please remove your medication from the dispenser." Or without a dispenser—"Mrs. Jones, it is time to take your blood pressure medication, please pass the prescription vial in front of the bar code/RFID Tag Reader."

The system will also be equipped with an RF 433 MHZ Receiver 6. This receiver will allow the user to add wireless sensors such as smoke, carbon monoxide, temperature, electricity, burglar alarm, keyless door entry, wireless perimeter alarm (a device to notify Customer Service Center or caregiver that the user has gone beyond prescribed boundaries) and panic buttons (Help I've Fallen Down) 17. Connection to the Customer Service Center of these sensors will be accomplished through an automatic dialer activated by the sensors or panic button generating a priority dial and alarm signal. All of these alarm sensors are currently available on the open market and the RFID receiver has been designed with custom ASIC devices to accept the sensors output. Other wireless sensors will be added but not limited to oxygen, electrocardiogram, renal and blood pressure.

Input of data to the Interactive Prescription Compliance System will be accomplished through use of RS232 type ports, RJ11 style telephone connectors and PCMCIA slots or ports 10. Other input devices are an Ethernet adapter or 56k Modem 2.19. These built in interconnects allow the System to communicate to the Customer Service Center or other sites through the PSTN, Cable, Ethernet (Lan & Wans) or the optional connection to a cellular phone 12.

An Interactive Audio/Video camera 16 will be installed on the Interactive Prescription Compliance System Set Top Box. This connection will be accomplished through custom logic and an RS232 type multifunction cable/connector, thus allowing the Customer Service Center and other individuals to view the user via the PSTN or Internet. Other viewing options can also be accommodated such as a hard wired system.

Referring to FIG. 6, the display pager 11 allows the user freedom to move away from the user's home or room. The user or Caregiver notifies the Customer Service Center of plans to be physically away from the Interactive Prescription Compliance System for an extended period of time. This notification can be accomplish via the conventional PSTN or optimally, a cell phone. If the user has a system using a dispenser, FIG. 1, the Customer Service Center then transmits the data stored in the Center for that user causing the dispenser, FIG. 1, to dispense the medication necessary for the period of time user will be away from the primary system. The pager-like device would be on line with the Customer Service Center and the Interactive Prescription Compliance System. Both the System and pager-like device would have the same telephone number. The pager-like device would be equipped with reprogrammable memory and battery operated. This feature allows the Customer Service Center, with prior user notification, to download the SIG (dosage and interval information) and alarm data and time to this pager-like device. This would allow the user to take the device and medication away from the home or room. The user would be notified by audio beeper-like signal or vibration and a text message displayed on the pager. Downloading of data and battery charging of the pager to the Interactive Prescription Compliance System would be accomplished via an RS232 port connecting the pager stand and the System. The pager stand would contain a battery charger, which would be connected by a line cord to a conventional AC consumer outlet.

Referring to FIG. 6, the cellular telephone has a dual function. The cellular telephone could be the primary voice and data links to the Interactive Prescription Compliance System. This would thereby eliminate the hard wired connection to the Customer Service Center and the PSTN. An additional function is off premise notification to the user of the SIG (dosage intervals). Compliance of prescription drug taking would occur by contacting the Customer Service Center to dispense the correct amount of packetized medication from the Interactive Prescription Compliance Drug Dispenser (FIG. 1). The user would then physically take the medications dispensed and the Customer Service Center would simply call the user's cellular phone and advise same which medication to take at the correct time. The user System without a dispenser would follow the same procedure but simply take the pill vials with them and calls would be placed by the Customer Service Center to the user's cellular telephone and advise which medication to take at the correct time.

Economics of scale require the Interactive Prescription Compliance System to be manufactured using multilayered and socketed Mother/Daughter Board techniques, using this procedure allows levels of service for the options available to the basic system. The basic system specifications and staffing for level of service options is thus defined.

HOME INTERACTIVE PRESCRIPTION COMPLIANCE AND LIFE SAFETY SYSTEM

Referring to FIG. 3.1, 3.2, 4.1 and 4.2, the patient's doctor writes prescription containing the following information: patient's name, doctor's name, drug name indicating whether or not generic replacement is acceptable, drug strength, drug quantity, SIG (dosage intervals) and amount paid. The pharmacist requires the following in addition to information provided on prescription form: patient's address, patient telephone number, date of birth and sex. The pharmacist creates the following information: Rx number, refill number, date and time sold. All of this information is entered into the pharmacy data entry workstation. This workstation is networked to the bar code label printer using an RS232 port and creates the label and unique barcode for the patient. The entire patient prescription data packet is sent to the pharmacy data processing center 3.3 and 4.3 and is compared to other prescriptions the patient may also be taking or has on file. If there are other prescriptions present in the data processing center, data base 3.3 and 4.3, for the same patient, drug interactions are possible because some patients have multiple doctors. If a drug interaction is found, the data processing center 3.3 and 4.3 then the established communication link satellite, PSTN, Lan or WAN, notifies filling pharmacist. This is an added precaution. If there are no drug interactions, the pharmacy system creates prescription label including a patient specific bar code. The new technology of RFID tags are created using the same procedure. Obviously the label is created but the read/write RFID tag is programmed by the RFID tag programmer present in the prescription filling pharmacy, 3.1, 3.2, 4.1 and 4.2. The prescription is then filled the label/bar code or label RFID tag are affixed to the vial, FIG. 6. The bar code or RFID tag will contain, but not be limited to, the patient's name and unique prescription number. Other patient information will be stored in the filling pharmacy data base.

The mail order pharmacy, 3.2 and 4.2, fills prescriptions following the identical procedures of the retail pharmacy. Two additional functions are performed at this site. First the filling of the dispenser with packetized medication is completed, including application of pharmacy bar coded label on RFID tag. Second, the mail order facility does exactly as described; delivers the pill vial or interactive drug dispenser to the patient's extended care address or home.

Nightly procedures for both the retail pharmacy and the mail order pharmacy is to download the prescription data from the pharmacy data entry work station to the store or mail order pharmacy server (3.1, 4.1, 3.2, 4.3). This data is then data compressed, packetized and transmitted to the data processing center (3.3 and 4.3) frame relay, POTS (plain old telephone system), LAN, WAN, and Satellite transmission lines could be used. The download to the data processing center occurs at off peak hours usually 2 am Central Standard time.

Continuing with FIG. 3.3 and 4.3, the data processing center is the central location for all patient, doctor, prescription, insurance, bar code or RFID tag data. This allows the modern pharmacy chain store and mail order facilities to secure nationwide and soon worldwide central data storage, thus service as the pharmacy drug information source for the Customer Service Center (3.4 and 4.4). The interactive communication link between the data processing center (3.3 and 4.3) and the Customer Service Center should be a dedicated T2 type or satellite connection. The data processing center (3.3. and 4.3) download all patient doctor prescription insurance, bar code or RFID tag information to the Customer Service Center (3.4 and 4.4) on a daily basis. The following is then received from the data processing center:

1. Patient's name, address, phone number, sex, data of birth
2. Doctor's name, address, phone number, other doctors' prescriptions
3. Prescription number
4. Bar code/RFID tag code
5. Number of refills
6. Drug type (generic ok)
7. Quantity
8. Date and time sold
9. Interactive Compliance Reminder (usually provided through a set top box)
10. Pager serial number
11. Accessory list
    a. Wireless alarms
    b. Interactive audio visual
    c. Cellular phone number
    d. Pager serial number
    e. Interactive Compliance Reminder Prescription Dispenser serial number (FIG. 1)
    f. Billing method (credit card, check or cash)
    g. Insurance company identification
    h. Medicare/Medicaid Continuing with FIG. 3.4 and 4.4, the Customer Service Center receives the patient pharmacist information and stores the data. The Customer Service Center contacts the user via PSTN lines and obtains the following information:

1. Patient's name, age, sex, prescription number
2. Doctor's name, address, telephone number
3. SIG, dosage amount and time of day
4. Number of refills
5. Drug type
6. Quantity
7. Date and time Prescription on bought or received
8. Interactive Prescription Compliance Set Top Box serial number
9. Primary care giver name, address's and phone number
10. Call list of other care givers
11. Accessory list
    a. Wireless alarms
    b. Interactive audio/visual
    c. Cellular phone number
    d. Pager serial number
    e. Interactive Prescription Compliance Dispenser serial number
    f. Billing method (credit card, check or cash)
    g. Insurance company
    h. Medicare/Medicaid After Customer Service Center conducts live interview with patient or caregiver, the data collected is entered in the main frame data bank and compared to the pharmacy data for errors. If none are found the Initialization Procedure for the Interaction System begins.

INITIALIZATION:

1. Determine user phone tone or pulse (dial 9)
2. PIN number assigned System Set Top Box
3. PIN number assigned to Drug Dispenser
4. Level of service
   a. Turn on wireless alarms, Interactive Audio/Video Pager, other monitoring devices (oxygen, renal, electrocardiogram)
5. PIN number other service provides
   a. Visiting nurse, meals on wheels, medical equipment suppliers. (This feature is extremely effective in eliminating Medicare/Medicaid fraud by requiring other service providers to log-in and log-out to identify service or goods provided. This is accomplished through the keyboeard or bar code/RFID tag reader on the Interactive Compliance Reminder Set Top Box.)
6. System test The Customer Service Center will license from Medispan or First Data, the pharmacological information such pill size, shape, color, drug, interaction/reaction and special ingestion instructions. This information will be sent to the user and displayed concurrently with the Compliance Alarm Message Signal. This information is identical to information contained in pharmacy providing the prescription.

Description of FIGS. 3 and 4—Home Interactive Prescription Compliance System Architecture with Compliance Console and Interactive Audio Visual Option and the Institutional Interactive Prescription Compliance System Architecture with Compliance Set Top Box and Interactive Audio Visual option.

Referring to FIGS. 3 and 4, after initalization is completed, the Interactive Prescription Compliance Set Top Box functions in an identical manner, whether in the users' home, assisted living center or retirement community. The initialized version of FIG. 4 may use a LAN or WAN.

More particularly, a flowchart of personal information required and data storage location can be set out in chart form. A suggested chart form is as follows:

| Customer Service Center | Data Processing Center |
|---|---|
| Data Processing Center data received | Doctor Name, address, phone number |
| | Patient Name, address, phone number |
| Telephone interview w/patient to recheck data processing center info, date/time prescription received, installation of system, Set Top Box pin number, number of primary caregiver, name, address, phone | Drug Name/quantity (generic) |
| | SIG dosage & intervals |
| | Number of refills |
| | Prescription number |
| | Date and time sold |
| | Dispenser bar code/RFID tag |
| Emergency phone numbers | Bar code or RFID tag code |
| service providers pin numbers, police, fire, hospital, etc. | Drug interaction/reaction check |
| | Serial number Set Top Box |
| Initialized Set Top Box and options | Options, wireless alarm, medical monitors, pager number, wireless phone number |
| System check | |
| Software updates | Supplier advertising |
| Options added/deleted | Pharmacological data Medispan/First Data |
| New drug regimens | |
| Source of all exception reports | Billing method (credit card, lease check, cash, Medicare, Medicaid) |
| Compliance - Insurance - Alarm - | |

-continued

| Customer Service Center | Data Processing Center |
|---|---|
| and Service Providers Level service letter sent to patient - caregiver | |
| Patient Room, Apt. or House | Pharmacy Retail or Mail Order |
| System installed | Doctor name, address, phone number |
| Telephone interview with customer service center - level of service checked | Patient name, address, phone number |
| | date of birth, sex |
| | Drug name, quantity, generic, SIG dosage and intervals |
| Patient - caregiver verifies all information | Number of refills |
| Method of payment | Prescription number |
| Patient participates in system check, bar code swipe- -RFID swipe | Refill number |
| | Date, time sold |
| Interactive Compliance Remainder | Bar Code or RFID Tag code |
| System fully functional | Drug interaction/reaction check |
| | Mail order (load medicines in optional dispenser or fill bar coded or RFID tag prescriptions) |
| | Options, wireless alarms, medical monitors, pager number, cell phone number |
| | Billing method (credit card, lease, check, cash, Medicare/Medicaid. |

Referring to FIG. 5, this is a block diagram of the information collected by the pharmacy data processing center and Customer Service Center. FIG. 5 also shows where the collected data resides in each facility. This graphically depicts how interactive and redundant the system is, thus assuring correct medication. Options such as wireless alarm, service provider PIN numbers also redundantly checked, as depicted here in FIG. 5. Any changes in drug regimen are downloaded from the Customer Service Center to the user's Interactive Prescription Compliance System. These changes are accomplished utilizing the PSTN and the user's system reprogramable memory.

Description of FIG. 5—Prescription vial bar coded or RFID tagged.

Referring to FIG. 5, the pill vial for prescription drugs is available in numerous sizes. This figure is intended to depict where the RFID tag might be affixed to the vial. In most instances the prescription or RX label is affixed to the vial body and contains the barcode if used in lieu of RFID tag. This figure as stated depicts a prescription drug vial. However, the RFID tag and prescription (RX) label with barcode could also be affixed to liquid containing bottles and squeezable toothpaste-like tubes.

Statistics for costs of long term care and age projections in Illinois are similar to the national figures. Those statistics may be summarized as follows.

Illinois Long-Term Care Facts

1997 United States Census Bureau Statistics

Long-Term care facts:

Almost half of Illinoisans aged 65 or older will eventually need long-term care. Such care could include in-home help with the activities of daily living, such as dressing or bathing, or it could include skilled medical attention given in a nursing home.

Illinois' average cost of one year of long-term care is $13,000 for in-home services and $36,500 for a nursing home, with inflation adding another 6% per year.

Projected Distribution of the Elderly Population by Age Percent of Elderly Population

| Age Group | 1985 | 2010 | 2035 | 2050 |
|---|---|---|---|---|
| 65 to 69 | 32.2 | 29.9 | 24.0 | 24.6 |
| 70 to 74 | 26.6 | 21.8 | 24.3 | 20.0 |
| 75 to 79 | 19.6 | 17.4 | 21.0 | 17.1 |
| 80 to 84 | 12.2 | 14.0 | 14.8 | 14.6 |
| 85 to Over | 09.4 | 16.9 | 16.0 | 23.7 |

A large multi-employer pension fund recently reported that their retirees for the first time ever, out number the active participants. This trend will continue to be seen in other pension funds in the future.

Compilation of statistics for costs of long term care and age projections in Illinois indicate the value of this system.

Using the state of Illinois facts, U.S. Census Bureau statistics and recent newspaper articles, the need for an Interactive Prescription Compliance and Life Safety Monitoring System is dramatically illustrated. The aging of Americans is accelerating at an alarming rate. Also accelerating at alarming rates are Medicare and Medicaid fraud and elderly care costs. These articles and statistics support the need for my invention.

What is claimed:

1. An interactive prescription compliance and personal safety system, requiring both a user of the system to respond to alarm signals generated by a customer service center, and the customer service center to respond to alarm signals generated by the user, the interactive system comprising:

A. a pharmacy data terminal being adapted to record personal and prescription information of the user;

B. a reader for a coding means on a prescription dispenser identifying at least one prescription taken by the user, the coding means being at least one selected from the group consisting of a bar code and a radio frequency identification tag;

C. the customer service center communicating with the pharmacy data terminal, the reader, and the user in order to create a permanent patient data base;

D. the customer service center providing electronic data storage and prescription information for the user and communicating with a data processing center, in order to provide prescription information;

E. the customer service center being connected to a prescription compliance alarm;

F. the prescription compliance alarm being connected to a dispenser for medication;

G. the reader including an activation means for the prescription compliance alarm adapted to signal use or non use of the dispenser and to cause a response to non use;

H. the activation means including at least one selected from the group consisting of a console receiving and displaying a prescription compliance message and an audio alarm;

I. the reader being adapted to read the coding means and being connected to the activation means; and J. the reader serving to deactivate the alarm when a proper medication code is provided.

2. The interactive prescription compliance and personal safety system of claim 1 further comprising:

A. the reader providing a display means, the display means being selected from the group consisting of liquid crystal display and a television screen;

B. the reader including an activating means for sounding an audio alarm;

C. the audio alarm providing an indication of when to take medication;

D. the audio alarm cooperating with the reader in order to provide an indication of whether medication is proper; and E. the reader informing the data processing center of compliance or non compliance.

3. The interactive prescription compliance and personal safety system of claim 2 further comprising:

A. the reader receiving information of medication by the user from the coding means;

B. the reader generating a signal; and

C. the reader sending the signal to the data processing center in order to verify medication being taken.

4. The interactive prescription compliance and personal safety system of claim 3 further comprising:

A. the reader receiving information of at least one service provider;

B. the data processing center using conventional communications links, accepting all required data for the user, and, creating a permanent patient data base;

C. the data processing center having prescription information of least one selected from the group consisting of dosage, time interval, and level of service options and accessories is stored;

D. the data processing center generating a prescription compliance alarm in order for the user to cause medication to be dispensed; and E. the data processing center generating a third-party alarm after a personal safety alarm is detected.

5. A method of providing interactive prescription compliance and life safety alarms for a user, the method comprising:

A. providing a patient prescription record for at least one medication and life safety profile in a database;

B. generating prescription compliance alarm from the profile and the database;

C. downloading the database through the compliance alarm to require the user to remove medication from a dispenser;

D. causing the user to pass the medication in front of reader;

E. generating a compliance signal to the data base in order to verify medication removal from the dispenser in order to indicate compliance; and F. recording the compliance in the database.

6. The method of claim 5 further comprising:

A. generating a life safety alarm signal;

B. transmitting the life safety alarm signal to the database thereby recording date, time, and nature of the safety alarm signal; and C. relaying the life safety alarm to a correct authority; and D. monitoring a service provider, an equipment provider and medical life support equipment.

7. The method of claim 6 further comprising:

A. providing an interactive audio and video system in a home of the user;

B. controlling the interactive audio and video system in a home of the user through a designated third party; and C. utilizing a home telephone number and assigning that number to a pager-like device in order to provide compliance alarms, which is stored and activated at appropriate medication times.

* * * * *